United States Patent [19]

Deutsch

[11] Patent Number: 4,925,925
[45] Date of Patent: May 15, 1990

[54] RADIOACTIVE RHENIUM LIGATED TO 2-HYDROXY ISOBUTYRIC ACID AND METHOD OF USE

[75] Inventor: Edward A. Deutsch, Cincinnati, Ohio

[73] Assignee: University of Cincinnati, Cincinnati, Ohio

[21] Appl. No.: 332,735

[22] Filed: Apr. 4, 1989

Related U.S. Application Data

[62] Division of Ser. No. 206,880, Jun. 15, 1988, Pat. No. 4,839,467.

[51] Int. Cl.$^5$ ............... C07F 13/00; C01G 47/00
[52] U.S. Cl. ..................... 534/10; 556/49; 556/50; 424/1.1
[58] Field of Search ............ 424/1.1; 534/10; 556/49, 50

[56] References Cited

U.S. PATENT DOCUMENTS

| | | | |
|---|---|---|---|
| 4,452,774 | 6/1984 | Jones et al. | 424/1.1 |
| 4,707,544 | 11/1987 | Jones et al. | 534/10 X |
| 4,778,672 | 10/1988 | Deutsch et al. | 534/10 X |

Primary Examiner—John S. Maples
Attorney, Agent, or Firm—Wood, Herron & Evans

[57] ABSTRACT

A composition of matter having the following general formula

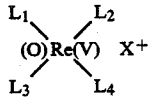

wherein L represents 2-hydroxy isobutyric acid. This composition of matter is useful in improving the reaction efficiency or yield when bonding rhenium to a chelating ligand preferably a polydentate sulfur, selenium, phosphorous or nitrogen ligand. This provides a method to bond radioactive rhenium to various chelating ligands for a radiopharmaceutical. Further, this also provides a method to bond a radioactive rhenium to a protein such as a monoclonal antibody. This in turn provides a method to provide beta emitting radiation to cancer cells.

3 Claims, No Drawings

RADIOACTIVE RHENIUM LIGATED TO 2-HYDROXY ISOBUTYRIC ACID AND METHOD OF USE

This is a division of application Ser. No. 206,880, filed on Jun. 15, 1988, now U.S. Pat. No. 4,839,467.

BACKGROUND OF THE INVENTION

Radiopharmaceuticals can be used for various purposes. Gamma emitting radiopharmaceuticals are typically used for imaging purposes. The gamma radiation is detectable with scintillation cameras There are many different gamma emitting radioisotopes such as, for example, technetium-99 m.

These, although useful for imaging purposes, are not useful for therapeutic purposes. The gamma radiation is so penetrating it does not have any substantial therapeutic applications. For radiopharmaceutical therapeutic applications, beta emitting isotopes are typically used. Beta radiation is less penetrating and deposits more energy in tissue and thus is used to destroy tissue, particularly cancerous tissue. Rhenium is one particularly well known source of beta emissions. Both rhenium-186 and rhenium-188 emit beta radiation as well as gamma radiation making them useful for detection purposes as well as treatment purposes.

The key to any treatment employing a radiopharmaceutical is localization of the radioactive material at the desired site. General application of a dose of beta radiation to the entire body would be more harmful than good. Therefore, it is extremely critical to ensure that a beta emitting radiopharmaceutical localizes at the selected site. To do this, various site specific compounds which are known to localize in particular tissue and organs are bonded to the radioactive beta emitting composition. The formed complex is then injected into the patient The radioactive material is then transported directly to the selected tissue or organ where it hopefully remains for a protracted period of time selectively destroying the diseased area with the emitted beta radiation.

Rhenium in certain respects provides the basis for very valuable and useful radiopharmaceuticals. Its availability in both the form of rhenium-186 and rhenium-188, which have different beta energies and physical half lives, makes it especially useful. Unfortunately, it is difficult to transfer a rhenium center from one ligand environment to another. Such transfers are necessary in formulations of rhenium labelled site specific compositions such as rhenium labelled antibodies and other rhenium labelled chelate compositions.

Rhenium-186 is obtained by neutron bombardment of rhenium-185. It is obtained in low concentrations. Therefore, a high reaction rate of the rhenium to the site specific composition is very critical. Rhenium-188 produced from a tungsten 188/rhenium 188 generator is obtained at especially low concentrations.

Certain reaction parameters such as high temperature can be used which favor transfer of the rhenium to the site specific composition. But unfortunately, most of these transfers require mild conditions which are not favorable to maximizing reaction efficiency. For example, when bonding a rhenium complex to a monoclonal antibody, the reaction conditions must be kept quite mild or otherwise the monoclonal antibody will be denatured.

In order to optimize certain of these transfer reactions from one metal ligand to another, intermediates have been formed. Ligands such as glucoheptonate have been useful with technetium chemistry. Unfortunately, there has been no good intermediate ligand useful to assist in the transfer reaction with rhenium.

SUMMARY OF THE INVENTION

The present invention is premised on the realization that 2-hydroxy isobutyric acid (also called methyllactic acid) is an effective transfer ligand for rhenium.

The rhenium ligated to 2-hydroxy isobutyric acid ligands forms an intermediate complex wherein the rhenium is stabilized in a reduced oxidation state presumably in the $+5$ state This rhenium-2 hydroxy isobutyric acid complex is still very reactive with other chelating ligands. This provides a reaction mechanism promoting a higher yield of a rhenium chelating ligand complex than for example when perrhenate is directly reacted with, or reduced in the presence of the chelating ligands. The chelating ligands most suitable for use in the present invention are bi, tri, tetra, and hexadentate ligands, particularly ligands having ligating moieties including the selenium and sulfur moieties as well as P, N, As and O moieties.

The invention is further premised on the realization that the following composition

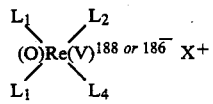

where L represents 2-hydroxy isobutyric acid can be used to provide a favorable mechanism to react rhenium with chelating ligands. Further, this invention is premised on the realization that the above composition can be used to react rhenium with monoclonal antibodies and other proteins and protein derivatives. The invention will be further appreciated in light of the following detailed description.

DETAILED DESCRIPTION

There are two preferred forms of radioactive rhenium—rhenium-186 and rhenium-188. Rhenium-186 is formed by radiating rhenium metal (rhenium-185) with strong neutron radiation, typically a neutron radiation having a flux of $10^{14}$ neutrons $cm^{-2}S^{-1}$. This is well known in the art and produces a mixture of both rhenium-186 and rhenium-185. The rhenium-185 predominates the solution and is referred to as the carrier.

The rhenium-186 metal is oxidized by strong oxidants such as hydrogen peroxide, nitric acid and the like. This forms the solution of perrhenate $ReO_4^{-1}$. This solution is then neutralized with a strong base such as ammonia or a strong acid such as hydrochloric acid or sulfuric acid The formed solution includes perrhenate-186 together with the bi-products of the oxidation.

An aqueous solution of perrhenate-188 can be obtained simply by eluting a tungsten-188 generator, or by following the above procedure using metallic rhenium-187.

To purify the perrhenate either 186 or 188, the aqueous crude solution of the radioactive perrhenate is treated with a lipophilic counter cation which is at least slightly soluble in water so that it can go into solution or associate with the perrhenate. Typically, tetrabutyl ammonium is used. The associated perrhenate is formed by simply adding the tetrabutyl ammonium to the crude aqueous solution containing the perrhenate. The solution is then added to a Sep-pak $C_{18}$ cartridge which is a reverse phase cartridge. The impurities can be removed by running water over the column and the perrhenate solution can be obtained in ethanol.

This is more fully disclosed in patent application Ser. No. 802,779 filed Nov. 27, 1985 entitled "Method of Isolating Radioactive Perrhenate or Pertechnetate from an Aqueous Solution". The disclosure in this application is incorporated herein by reference.

The obtained radioactive perrhenate is then reacted with 2-hydroxy isobutyric acid in the presence of a mild reducing agent such as stannous chloride or sodium borohydride. This reaction is conducted at elevated temperatures, generally at 50-100° C. under anaerobic conditions. For purposes of the present invention, an extreme excess (about 100,000 fold molar excess) of 2-hydroxy isobutyric acid should be employed. Following the reaction, the mixture is cooled to room temperature.

More particularly, a solution of rhenium-186 tetrabutyl ammonium perrhenate is obtained at a concentration of 0.04 milligram of rhenium in 2 milliliters of ethanol. 200 microliters of the perrhenate solution is diluted with 1200 microliters of water and deaerated. 20 milligrams of stannous chloride was dissolved in a deaerated solution of 450 milligrams of 2-hydroxy isobutyric acid in 0.6 milliliters of water. 400 microliters of the stannous chloride 2-hydroxy isobutyric acid solution is combined with the solution containing the perrhenate under anaerobic conditions. This is heated for 20 minutes at about 75° C. in a borosilicate vial capped with a teflon lined cap. This is sufficient to cause the 2-hydroxy isobutyric acid to react with the perrhenate.

Following this reaction, the mixture is cooled down to room temperature by placing it for about 10 minutes in a water bath.

The solution at this point has a pH of about 2. Before further reaction, it may be desirable to adjust the pH of this solution. Accordingly, the pH is preferably adjusted to 5 with 10 normal potassium hydroxide. The pH can then be raised again to about 8 with 20% potassium orthophosphate generally under anaerobic conditions. This two-step neutralization permits control of the neutralization. If a strong base, such as potassium hydroxide were used to completely neutralize the solution, the neutralization cannot be easily controlled.

The complex is difficult to isolate for characterization. Although not bound by any particular scientific theory, it is believed that the ligated rhenium 2-hydroxy isobutyric acid has the following general formula $$(O)Re(V)(L)_4^- X^+$$

wherein L represents 2-hydroxy isobutyric acid and the Re is Re-188 or Re-186.

X represents a pharmaceutically acceptable cation such as an alkali metal generally Na+.

The 2-hydroxy isobutyric acid tends to stabilize the rhenium in the +5 state. Although stabilized, it is very reactive with other chelating ligands.

The chelating ligands in the present invention are multidentate ligands wherein the ligands chelate via an atom selected from the group consisting of selenium, sulfur, phosphorous, arsenic, nitrogen and oxygen. Further, these may be chelated to a group such as an isonitrile group wherein the bond between the ligand and the rhenium center is shared between the carbon and nitrogen atoms.

These multidentate ligands can be bidentate, tridentate, tetradentate or even hexadentate ligands.

Preferred chelating ligands are thiolate containing ligands and nitrogen containing ligands such as the following:

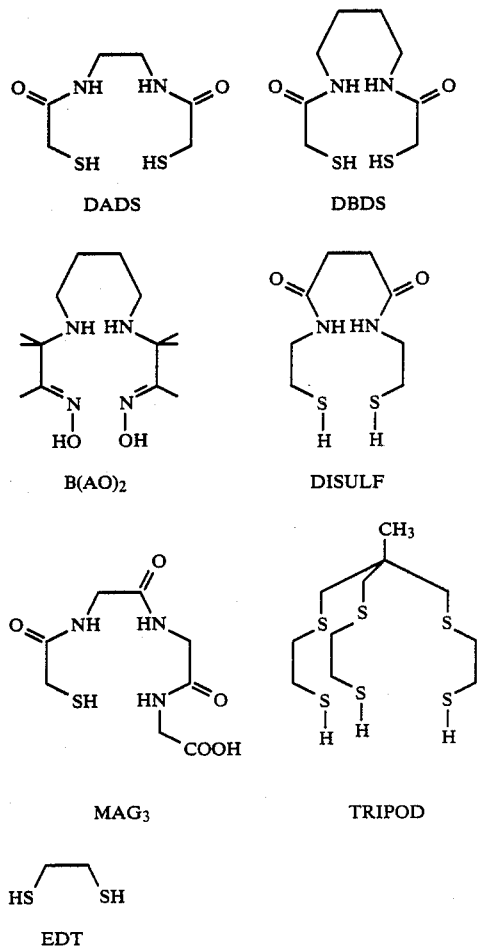

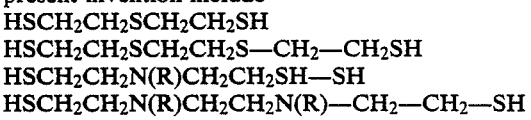

EDT

Other sulfur ligands particularly suited for use in the present invention include
$HSCH_2CH_2SCH_2CH_2SH$
$HSCH_2CH_2SCH_2CH_2S—CH_2—CH_2SH$
$HSCH_2CH_2N(R)CH_2CH_2SH—SH$
$HSCH_2CH_2N(R)CH_2CH_2N(R)—CH_2—CH_2—SH$ Phosphorous, nitrogen and arsenic ligands include:
DMPE$((CH\ )_2P—CH_2CH_2—P(CH_2)$
diars $(O—C_6H_4(As(CH_3)_2)_2$
diphos $((C_6H_5)_2—CH_2CH_2—P(C_6H_{52})$
tris (1-pyrazolyl)borato
porphyrin
bipyridine
terpyridine
cyclam, 1,4,8,11-tetraazacylotetra decane and derivatives
tetraphos $P(CH_2CH_2P\ (C_6H_5)_2)_3$
DAE $((C_6H_5)_2As—CH_2CH_2NHCH_2CH_2NH_2)$
DIEN $(H_2N—CH_2CH_2NHCH_2CH_2NH_2)$
TRIEN $H_2NCH_2CH_2NHCH_2CH_2NHCH_2CH_2NH_2$
1,2-bis(ditoluylphosphino)ethane 1,2-bis(di(trifluoromethyl)phosphino)ethane
1,2-bis(dimethylphosphino)-1,1-difluoroethane
1,2-bis(dimethylphosphino)-1-fluoroethane
1,2-bis(dimethylphosphino)propane
1,2-bis(di(trifluoromethyl)phosphino)-1,1,2,2-tetrafluoroethane
1,2-bis(di(trifluoromethyl)phosphino)propane
2,3-bis(di(trifluoromethyl)phosphino)butane
1,2-bis(di(trifluoromethyl)phosphino)butane
1,3-bis(dimethylphosphino)butane
1,3-bis(dimethylphosphino)propane
1,3-bis(di(trifluoromethyl)phosphino)propane
1,2-bis(dimethylphosphino)-1,1-dichloro-2,2-difluoroethane
1,2-bis(diethylphosphino)ethane
1,2-bis(diisopropylphosphino)ethane
1,2-bis(dipropylphosphino)ethane
1-dimethylphosphino-2-diisopropylphosphinoethane
1,2-bis(diisobutylphosphino)ethane
1-dimethylphosphino-2-dimethylarsinoethane Alkyl diphosphonate (ethylene diphosphonate) Also, isonitrile ligands such as those disclosed in U.S. Pat. No. 4,452,774 such as t-butylisonitrile can be used.

Other suitable ligands are disclosed in European Patent Application No. 86100360.6 filed Jan. 13, 1986 entitled "Metal Radionuclide Labelled Proteins for Diagnosis and Therapy." These ligands are diamine dithiol ligands ($N_2S_2$) such as N N'-bis(benzoylmercaptoacetyl)-3,4-diamino butyrate. Phosphonate containing ligands particularly suitable for use in the present invention are disclosed in European Patent Application No. 86201074.1 filed June 20, 1986 entitled "Diphosphonate Derivatized Macromolecules." This reference discloses diphosphonates such as ethylene diphosphonate bonded to a macro molecule such as a polymer, protein or antibody by a linking moiety such as a carbamate moiety or diazo moiety. Such diphosphonates include phenylisothiocyanate diphosphonate, aryl sulfanyl halide diphosphonate, N-carboxyanhydride diphosphonate, imidate diphosphonate, quinone substituted diphosphonate and aldehyde diphosphonate. Further compositions include 2,3-dimercaptoacetamidopropanoate. Also, the 2-chloro-4-nitro, 2,4,5-trichloro, and 2,3,5,6-tetrafluoro and 1-hydroxybenzotrizole derivatives of 4,5-dimercaptoacetamidopentanoate are also suitable for use in the present invention.

To form the bond between the rhenium and the chelating ligands discussed above, the ligand (2 molar excess) is added to the neutralized solution of (O)-Re(V)(L)$_4$$^-$ and allowed to react at room temperature over a period of about an hour. The solution should then be suitable for purification and/or injection into an individual for appropriate purposes.

The preparation of the rhenium tetra(2-hydroxy isobutyric acid) will be appreciated further in light of the following detailed description which uses rhenium-188 in combination with ammonium perrhenate as a carrier.

EXAMPLE 1

The following solutions were prepared:
$2 \times 10^{-2}$M ammonium perrhenate and methanol;
Re-188 tetrabutyl ammonium perrhenate and methanol about 1 mCi/mL;
20 milligrams of stannous chloride, 450 milligrams of 2-hydroxy isobutyric acid in 0.6 milliliters of water; and
$4 \times 10^{-2}$ M ethane dithiol in a deaerated 50% solution of ethanol and water.

1 microliter of ammonium perrhenate was combined with 200 microliters of the tetrabutyl ammonium perrhenate-188 and 1200 microliters of water. This solution was then deaerated.

400 microliters of the solution of stannous chloride and 2-hydroxy isobutyric acid was combined with the perrhenate solution under anaerobic conditions. The mixture was placed in a borosilicate vial capped with a teflon lined cap and heated for 20 minutes at 75° C. The mixture was then cooled to room temperature (10 minutes in a water bath at room temperature).

2 microliters of the ethane dithiol and deaerated ethanol and water were then added to the borosilicate vial. The pH was adjusted to 5 with 10 normal potassium hydroxide and then to 8 with 20% potassium hydroxide (about 200 microliters) under anaerobic conditions. The final concentration of the reagents are rhenium $2 \times 10^{-5}$M, ethane dithiol $4 \times 10^{-5}$M ($2 \times$ excess assuming 2 thiol molecules per 1 rhenium atom) isobutyric acid 1.4 molar and stannous chloride $3 \times 10^{-3}$M.

After 1 hour from the pH adjustment, the sample was analyzed with HPLC with the use of a C-18 5 micron reverse phase column using 25% methanol/0.01M sodium phosphate pH 7 as a mobile phase and flow rate of 1 milliliter per minute. The chromatogram shows more than 90% yield of rhenium 1,2 ethane dithiol chelate.

The rhenium 2-hydroxy isobutyric acid composition is useful in formation of a variety of different compositions having a variety of different utilities. For example, the rhenium composition of the present invention can be used to successfully conjugate rhenium to a macromolecule such as a water soluble polymer for radiosynovectomy according to the method disclosed in *Nucl. Med. Biol.*, Vol. 15, 2, pages 151-156, 1988. According to this method, the ligand will be a chelating ligand bonded to a macromolecule such as proteins, polysaccharides, polyacrylamide, polymethacrylate, polyhydroxy alkyl methacrylate, polyvinyl alcohol, polymaleic anhydride, polymaleate, polyamide, polyethyleneamine, polyethylene glycol, polypropylene glycol and so on. These macromolecules are bonded to a chelating ligand such as ethylene dithiol or a diphosphonate ligand. The composition is formed by simply combining the chelating ligand (bonded to the macromolecule) to the rhenium tetra (2-hydroxy isobutyric acid) composition. This is allowed to stand at room temperature for an hour. The obtained solution is then intra-articularly injected. The macromolecule portion of the chelating ligand prevents the radiopharmaceutical from leaking from the treated joint providing radiation treatment only in that joint.

The rhenium tetra (2-hydroxy isobutyric acid) composition can also be used to radiolabel monoclonal antibodies. According to this method, the rhenium is chelated to a chelating ligand which contains a reactive side group adapted to bond to a specific amino acid. Such chelating ligands are well known. For example, 2,3,5,6-tetrafluoro phenyl, 2,3,-dimercaptoacidomidopropanate reacts with glycine, asparic acid, glutamic acid and arginine at a pH of 8.5. This general reaction of the chelating ligand to monoclonal antibody is shown, for example, at paper 118, page 269 of the Sixth International Symposium on Radiopharmaceutical Chemistry.

This complex of the present invention can also be used to bond rhenium to diethylenetriaminepentaacetic acid (dtpa) which is bonded to a monoclonal antibody or an antibody fragment such as F(AB')$_2$. A method of bonding the dtpa to the antibody is generally disclosed in Paik, U.S. Pat. No. 4,652,440, the disclosure of which is incorporated herein by reference.

In all of these reactions, the rhenium tetra (2-hydroxy isobutyric acid) facilitates the conjugation between the rhenium and the chelating ligand. The chelating ligand in turn is site specific for particular applications and it takes the rhenium to the desired location. In the case of radiation synovectomy, the ligand maintains the rhenium in its appropriate location.

With respect to antibodies, the chelating ligand is simply a ligand having a site specific reactive ester such as the acid ester of tetrafluoro phenyl which is an activated ester group adapted to react to an amine group on an antibody. This reaction binds the chelating ligand and thus the rhenium to the antibody providing for direct physical attachment of the rhenium to the appropriate cancer cell that the antibody is directed against. Alternately this ligand can be bonded first to the antibody or fragment and then reacted with the rhenium intermediate. This facilitates providing the radiation dosage directly at the diseased cell. Accordingly, the present invention can be used in any application where facilitation of bonding of rhenium to a chelating ligand is appropriate.

The preceding has been a description of the preferred embodiment of the present invention as well as generally how to practice the present invention. The limits of this invention, however, are defined by the appended claims wherein I claim:

I claim:

1. A method of bonding rhenium 186 or rhenium-188 to a chelating ligand comprising forming a complex $Re(O)L_1-L_4-X^+$ wherein $L_1-L_4$ represent 2-hydroxy isobutyric acid and X is an anion and reacting said $Re(O)L_1-L_4-X^+$ with a chelating ligand selected from the group consisting of multidentate ligands having chelating moieties selected from the group consisting of sulfur, nitrogen, phosphorous, arsenic, selenium, isonitrile, oxygen and combinations thereof.

2. The method claimed in claim 1 wherein said chelating ligands are thiolate ligands.

3. The method claimed in claim 1 wherein said chelating ligands are selected from the group consisting of tetradentate ligands, tridentate ligands, and hexadentate ligands.

* * * * *